(12) United States Patent
Kuromaru et al.

(10) Patent No.: US 6,596,537 B1
(45) Date of Patent: Jul. 22, 2003

(54) HUMAN INTERLEUKIN-6 RECEPTOR EXPRESSION INHIBITOR

(75) Inventors: Kiyonori Kuromaru, Gotenba (JP); Yasuo Koishibara, Gotenba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 101 days.

(21) Appl. No.: 08/849,949

(22) PCT Filed: Dec. 15, 1995

(86) PCT No.: PCT/JP95/02587

§ 371 (c)(1),
(2), (4) Date: Jun. 16, 1997

(87) PCT Pub. No.: WO96/18416

PCT Pub. Date: Jun. 20, 1996

(30) Foreign Application Priority Data

Dec. 16, 1994 (JP) .............................................. 6-313167
Aug. 18, 1995 (JP) .............................................. 7-210739

(51) Int. Cl.[7] .......................... C07H 21/04; C12N 15/00
(52) U.S. Cl. ..................... 435/375; 536/24.1; 536/24.5; 536/23.1
(58) Field of Search .............................. 536/23.1, 24.1, 536/24.5; 435/375

(56) References Cited

U.S. PATENT DOCUMENTS 5,585,479 A * 12/1996 Hoke et al. ................. 536/24.5

FOREIGN PATENT DOCUMENTS

JP          2-88898          11/1990

OTHER PUBLICATIONS

Stull et al "Antigrn, Ribozyme and Aptamer Nucleic Acid Drugs: Progress and Prospects" Pharmaceutical Research vol. 12(4)465–483, 1995.*

A.R. Thierry et al., "Overcoming Multidrug Resistance in Human Tumor Cells Using Free and Liposomally Encapsulated Antisense Oligodeoxynucleotides", Biochem. Biophys. Res. Commun. (Feb. 1993), vol. 190, p. 952–960.

Jun Fukita et al. "Study and Clinical Application of Cancer Gene in Nephrocyte Cancer: Trial of Anti–interleukin 6 Therapy of Nephrocyte Cancer: Trial of Anti–interleukin 6 Therapy of Nephrocyte Cancer", Urological Bulletin (Nov., 1992) vol. 38, p. 1333–1336.

* cited by examiner

Primary Examiner—Sean McGarry
(74) Attorney, Agent, or Firm—Burns, Doane, Swecker & Mathis, LLP

(57) ABSTRACT

The present invention discloses an expression inhibitor of human interleukin-6 receptor (human IL-6R) comprising as its active ingredient an antisense oligonucleotide derivative that hybridizes to a region of at least 9 to 30 consecutive nucleotide sequences that contains a nucleotide sequence of a portion being able to form a loop structure of mRNA that codes for human IL-6R.

21 Claims, 2 Drawing Sheets

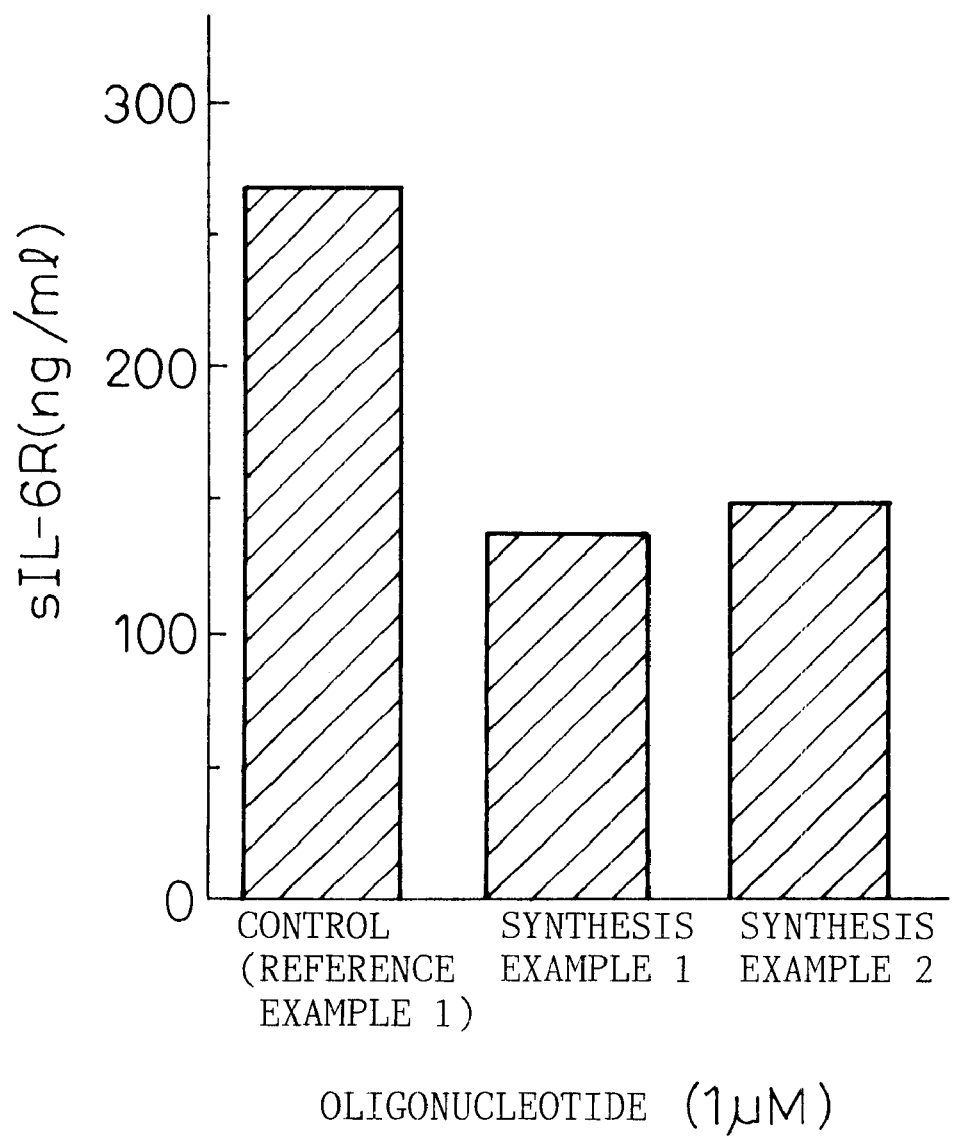

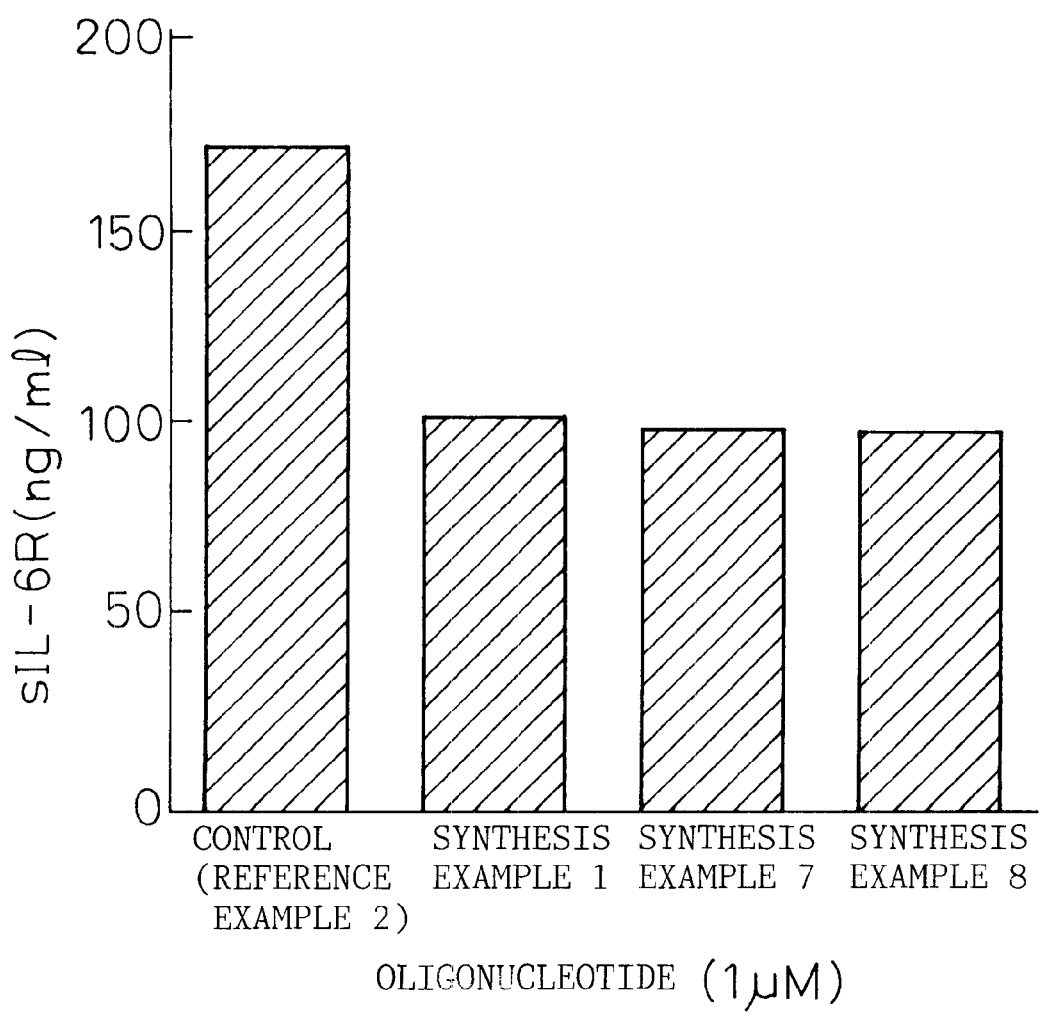

HUMAN INTERLEUKIN-6 RECEPTOR EXPRESSION INHIBITOR

TECHNICAL FIELD

The present invention relates to an antisense oligonucleotide derivative which is useful as a pharmaceutical that inhibits the expression of human interleukin-6 receptor (IL-6R).

BACKGROUND ART

Human interleukin-6 (human IL-6) is a cytokine that was cloned as a factor that induces the final stage of differentiation of B cells to antibody-producing cells (Kishimoto, T. et al., Blood 74, 1–10, 1989). At present, it is known to have various effects, including induction of acute phase protein in the liver (Kishimoto, T. et al, Blood 74, 1–10, 1989).

In addition, IL-6 has been reported to be produced not only in lymphoid cells, but also in fibroblasts, vascular endothelial cells, urinary bladder carcinoma cell strain T24 and glioblastomas (Kohase, M. et al., J. Cell Physio. 132, 271–278, 1978; Meir E. V. et al., Cancer Res. 50, 6683–6688, 1990). Moreover, it also has a diverse range of target cells (Kishimoto, T. et al., Blood 74, 1–10, 1989).

In recent years, IL-6 has been reported to function as autocrine growth factor in myeloma cells (Kawano, M. et al., Nature, 332, 83–85, 1988). Moreover, similar reports have been made with respect to nephrocytoma (Miki, S. et al., FEBS Letter 250, 607–610, 1989).

On the other hand, the signal for cell growth or differentiation by human IL-6 is known to be transmitted to cells by means of human IL-6R and glycoprotein gp130 present on the cell surface (Taga, T. et al., Cell 58, 573–581, 1989; Hibi, M. et al., Cell 68, 1149–1157, 1990).

In recent years, as a method for suppressing the function of a gene that is the cause of a particular disease, the use of a oligonucleotide complementary to mRNA transcribed from DNA (antisense oligonucleotide) has been proposed to inhibit expression of said protein (Murakami, Chemistry 46, 681–684, 1991).

Moreover, as a means of eliminating problems such as the life, stability and rate of uptake into cells of antisense oligonucleotides, modified antisense oligonucleotides, such as methylphosphonate derivatives, in which the oxygen of a phosphate group of the nucleotide is substituted with a methyl group, and phosphorothioate derivatives, in which the oxygen group is substituted with sulfur (Murakami, Chemistry 46, 681–684, 1991) are known. In actuality, these antisense oligonucleotides have been observed to inhibit synthesis of viral protein (Agris, C. H. et al., Biochemistry, 25, 6268–6275, 1986).

Based on this concept, Levy, Y. et al. confirmed that the growth of myeloma cell strains, for which human IL-6 is a growth factor, is inhibited as a result of translation of mRNA for IL-6 being inhibited by antisense oligonucleotide (Levy, Y. et al., J. Clin. Invest., 88, 696–699, 1991).

However, an antisense oligonucleotide derivative that significantly inhibits expression of IL-6R in various cells in which IL-6R is expressed is not known.

DISCLOSURE OF THE INVENTION

Thus, the present invention is intended to provide an antisense oligonucleotide derivative that inhibits the expression of human IL-6R.

More specifically, the present invention provides a human IL-6R expression inhibitor comprising an antisense oligonucleotide derivative corresponding to at least nine consecutive nucleotide sequences that contain the nucleotide sequence of the portion that has a high possibility of being able to form a loop structure of mRNA that codes for human IL-6R.

BRIEF DESCRIPTION OF THE DRAWINGS

FIG. 1 is a graph indicating that the antisense oligonucleotide derivatives of the present invention in Example 1 (SEQ ID NOs: 2 and 3) inhibit expression of soluble IL-6R.

FIG. 2 is a graph indicating that the antisense oligonucleotide derivatives of the present invention in Example 1 (SEQ ID NOs: 2, 9 and 10) inhibit expression of soluble IL-6R.

MODE FOR CARRYING OUT THE INVENTION

The inventors of the present invention searched for those nucleotide sequences considered to easily form a loop structure in terms of free energy and structural factors in human IL-6R mRNA using commercially available computer software for calculating free energy (e.g., Genetyx, Secondary Structure Search and Hairpin Loop-Stem Parts Search manufactured by Software Development Co., Ltd.). When an antisense oligonucleotide derivative containing that loop structure was synthesized, it was found to inhibit expression of human soluble IL-6R (sIL-6R), thereby leading to completion of the present invention.

In the preferable mode of the present invention, antisense oligonucleotide derivatives corresponding to sequences of 9 to 30, and more preferably, 12 to 25 consecutive nucleotides that contain a nucleotide sequence being able to form a loop structure of mRNA that codes for human IL-6R.

The "antisense oligonucleotide" described here refers not only to that in which all the nucleotides corresponding to nucleotides that form the prescribed region of DNA or mRNA are complementary, but also to that in which some mismatches are present provided the DNA or mRNA can be stably hybridized with the oligonucleotide.

The nucleotide sequence of the cDNA for human IL-6R is as follows (see, for example, Japanese Unexamined Patent Publication No. 2-288,298 or Science, 241, 825–828 (1988): (SEQ ID NO: 1).

Of the nucleotide sequences, nucleotide sequences of the antisense oligonucleotide derivative of the present invention are those which can be suitably selected from sequences of consecutive nucleotide sequences that are able to form a loop structure found according to the above-mentioned method.

Here, the portion that is able to form a loop structure of mRNA refers to the portion in which intramolecular hydrogen bonds of mRNA hardly exist, and often exist as a single strand state.

More specifically, a portion that often exists as a single strand state can be found, when the mRNA adopts a stable structure, using the above-mentioned computer software.

In the present invention, examples of portions that are able to form the above-mentioned loop structure in the nucleotide sequence shown in SEQ ID NO: 1 include around 640 to 685, 770 to 810, 1340 to 1375, 460 to 475, 535 to 560 as well as around 925 to 960 and 815 to 840.

Thus, the oligonucleotide of the present invention is an oligonucleotide comprising, for example, at least nine consecutive nucleotides in the above-mentioned region.

According to one embodiment of the present invention, an expression inhibiting oligonucleotide has the nucleotide sequence complementary to the nucleotide sequence of the codons that codes for, for example, the sequence from Ala at position 75 to Leu at position 81 in SEQ ID NO: 1, namely 5'-AGCCTCCTTCCCATGCCAGC-3' (SEQ ID NO: 2).

Other examples include an oligonucleotides having a nucleotide sequence complementary to the nucleotide sequence of the codons that code for the sequence from Leu at position 127 to Glu at position 133, namely 5'-CTCACAAACAACATTGCTGA-3' (SEQ ID NO: 3), that having a nucleotide sequence complementary to the nucleotide sequence of the codons that code for the sequence from His at position 70 to Met at position 77, namely 5'-TGCCAGCCCATCTGCTGGGG-3' (SEQ ID NO: 4), that having a nucleotide sequence complementary to the nucleotide sequence of the codons that code for the sequence from Val at position 34 to Asp at position 41, namely 5'-CTCCTGGCAGACTGGTCAGC-3' (SEQ ID NO: 5), that having a nucleotide sequence complementary to the nucleotide sequence of the codons that code for the sequence from Gln at position 118 to Lys at position 124, namely 5'-TTCCGGAAGCAGGAGAGCTG-3' (SEQ ID NO: 6), that having a nucleotide sequence complementary to the nucleotide sequence of the codons that code for Pro at position 164 to Glu at position 170, namely 5'-TCCTGGGAATACTGGCACGG-3' (SEQ ID NO: 7), that having a nucleotide sequence complementary to the nucleotide sequence of the codons that code for the sequence from Ala at position 75 to Leu at position 82, namely 5'-GCAGCCTCCTTCCCATGCCA-3' (SEQ ID NO: 9), and that having a nucleotide sequence complementary to the nucleotide sequence of the codons that code for the sequence from Trp at position 74 to Arg at position 80, namely 5'-CTCCTTCCCATGCCAGCCCA-3' (SEQ ID NO: 10).

The structure in the case wherein the oligonucleotide derivative used in the present invention is a deoxyribonucleotide is as shown in Chemical Structure 1 wherein X may independently be oxygen (O), sulfur (S), a lower alkyl group or a primary or secondary amine. Y may independently be either oxygen (O) or sulfur (S). B is selected from among either adenine, guanine, thymine or cytosine, and is usually an oligonucleotide complementary to DNA or mRNA that codes for human IL-6 receptor. R is independently hydrogen, a dimethoxytrityl group or a lower alkyl group. n is an integer from 7 to 28.

Preferable examples of oligonucleotide derivatives include not only unmodified oligonucleotides, but also modified oligonucleotides. Examples of these modified forms include the above-mentioned methylphosphonate type or ethylphosphonate type of lower alkylphosphonate-modified forms, other phosphorothioate-modified forms and phosphoramidate modified forms.

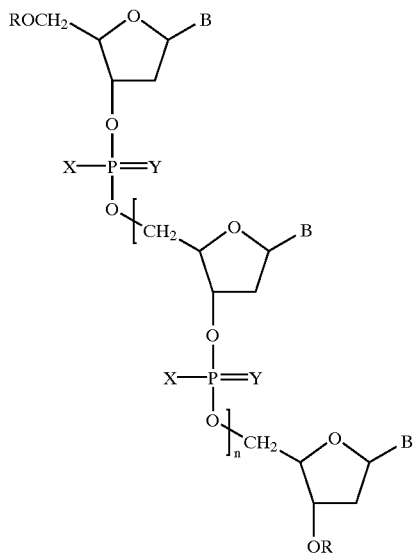

Chemical Structure 1

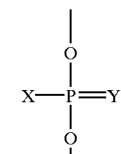

Example of

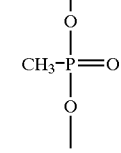

Methylphosphonate

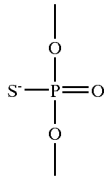

Phosphorothioate

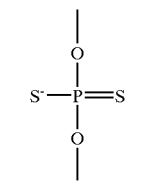

Phosphorodithioate

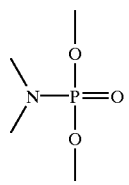

Phosphoramidate

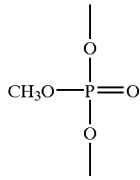

Phosphate triester

These oligonucleotide derivatives can be obtained by conventional methods as described below.

The oligonucleotide in which X and Y are O in the Chemical Structure 1 can be easily synthesized by a commercially available DNA synthesizer (e.g., that manufactured by Applied Biosystems).

Examples of synthesis methods that can be used to obtain this oligonucleotide include solid phase synthesis using phosphoroamidite and solid phase synthesis using hydrogen phosphonate.

For example, see T. Atkinson, M. Smith, in Oligonucleotide Synthesis: A Practical Approach, ed. M. J. Gait, IRL Press, 35–81 (1984); M. H. Caruthers, Science, 230, 281 (1985); A. Kume, M. Fujii, M. Sekine, M. Hata, J. Org. Chem., 49, 2139 (1984); B. C. Froehler, M. Matteucci, Tetrahedron Lett., 27, 469 (1986); P. J. Garegg, I. Lindh, T. Regberg, J. Stawinski, R. Stromberg, C. Henrichson, ibid., 27, 4051 (1986); B. S. Sproat, M. J. Gait, in Oligonucleotide Synthesis: A Practical Approach, ed. M. J. Gait, IRL Press, 83–115 (1984); S. L. Beaucage and M. H. Caruthers, Tetrahedron Lett., 22, 1859–1862 (1981); M. D. Matteucci and M. H. Caruthers, Tetrahedron Lett., 21, 719–722 (1980); M. D. Matteucci and M. H. Caruthers, J. Am. Chem. Soc., 103, 3185–3191 (1981).

Phosphate triester-modified forms, in which X is a lower alkoxy group, can be obtained by conventional methods, an example of which is treated an oligonucleotide obtained in chemical synthesis with a tosylchloride solution of DMF, methanol and 2,6-lutidine (Moody, H. M., et al., Nucleic Acids Res., 17, 4769–4782 (1989)).

Alkylphosphonate-modified forms, in which X is an alkyl group, can be obtained using conventional methods, an example of which uses phosphoramidite (M. A. Dorman, et al., Tetrahedron, 40, 95–102 (1984); K. L. Agarwal and F. Riftina, Nucleic Acids Res., 6, 3009–3024 (1979)).

Phosphorothiate-modified forms, in which X is S, can be obtained by conventional methods, examples of which include solid phase synthesis using sulfur (C. A. Stein, et al., Nucleic Acids Res., 16, 3209–3221 (1988), or solid phase synthesis using tetraethylthiuram disulfide (H. Vu and B. L. Hirschbein, Tetrahedron Letters, 32, 3005–3008 (1991)).

Phosphorodithioate-modified forms, in which X and Y are both S, can be obtained by, for example, solid phase synthesis by converting bisamidite to thioamidite and reacting with sulfur (W. K.-D. Brill, et al., J. Am. Chem. Soc., 111, 2321–2322 (1989)).

Phosphoramidate-modified forms, in which X is a primary or secondary amine, can be obtained by, for example, solid phase synthesis by treating hydrogen phosphonate with a primary or secondary amine (B. Froehler, et al., Nucleic Acids Res., 16, 4831–4839 (1988). Alternatively, the above-mentioned modified forms can also be obtained by oxidizing amidite with tert-butylhydroperoxide (H. Ozaki, et al., Tetrahedron Lett., 30, 5899–5902 (1989)).

Purification and confirmation of purity can be performed with high-performance liquid chromatography or polyacrylamide gel electrophoresis. Confirmation of molecular weight can be performed with electrospray ionization mass spectrometry or fast atom bombardment mass spectrometry. The antisense oligonucleotide derivative of the present invention may be synthesized in any manner and be of any origin provided it has a sequence that hybridizes with the nucleotide sequence of DNA or mRNA that codes for human IL-6R.

The antisense oligonucleotide derivative of the present invention acts on human IL-6R producing cells so that the derivative bonds to DNA or mRNA that codes for human IL-6R so as to inhibit its transcription or translation, and ultimately resulting in suppressing the effect of human IL-6 as a result of inhibiting expression of human IL-6R. Examples of the effects of human IL-6 inhibited by the antisense oligonucleotide derivative of the present invention include platelet proliferation effects, antibody production enhancing effects, acute phase protein inducing effects, tumor cell growth effects and neuron differentiation effects.

Thus, the antisense oligonucleotide derivative of the present invention is considered to be effective in the treatment of diseases caused by these effects, examples of which include carcinomas such as kidney cancer, myeloma, Lennert's T lymphoma and Kaposi's sarcoma, autoimmune diseases such as chronic rheumatoid arthritis, mesangium proliferative nephritis, psoriasis, carcinomatous cachexia and endotoxin shock in infections.

The antisense oligonucleotide derivative of the present invention can be mixed with suitable carriers that are inactive relative to said derivative to prepare external preparations such as liniments and poultices.

In addition, the antisense oligonucleotide derivative of the present invention can also be formulated to tablets, powders, granules, capsules, liposome capsules, injections, liquids, nasal drops as well as freeze-dried products by adding vehicles, isotonic agents, solubility assistants, stabilizers, preservatives or analgesics. These preparations can be prepared in accordance with conventional methods.

The antisense oligonucleotide derivative of the present invention can be applied either directly to the afflicted area on the patient, or eventually reach the afflicted area by intravenous administration and so forth. Moreover, antisense inclusion materials can also be used to improve duration and membrane permeability. Examples of these include liposomes, poly-L-lysine, lipids, cholesterol, lipofectin and their derivatives.

The dose of the antisense oligonucleotide derivative of the present invention can be suitably adjusted according to the status of the patient, and used in a preferable amount. For example, it can be administered at a dose within the range of 0.1 to 100 mg/kg, and preferably within the range of 0.1 to 50 mg/kg.

The following provides a detailed explanation of the present invention through its embodiments.

EXAMPLES

Synthesis Example 1

Synthesis of 5'-AGCCTCCTTCCCATGCCAGC-3' (SEQ ID NO: 2) (Phosphorothioate-modified Form)

The methoxytrityl group of 5'-dimethoxytrityl-2'-deoxycytidine, in which the 3'-hydroxy group was bonded to the support medium, was deprotected by trichloroacetate, and 5'-dimethoxytrityl-2'-deoxyguanosine β-cyanoethylphosphoramidite was condensed with its 5'-hydroxy group by tetrazole. After sulfiding the phosphorous with tetraethylthiuram disulfide, the unreacted 5'-hydroxy group was acetylated with acetic anhydride and dimethylaminopyridine.

Deprotection, condensation, sulfidation and acetylation were repeated in a similar manner. The final 5'-dimethoxytrityl-2'-deoxyadenosine β-cyanoethylphosphoramidite derivative was condensed and the resulting 20-mer phosphorothioate-modified form following sulfidation (the above-mentioned processes were performed with the Model 381A DNA synthesizer manufactured by Applied Biosystems) was separated from the support medium with 2 ml of concentrated aqueous ammonia along with removing the cyanoethyl group from the phosphorous and additionally removing the protection groups attached to adenine, guanine and cytosine.

The 5'-dimethoxytrityl protection group was removed from the resulting 5'-dimethoxytrityloligonucleotide phosphorothioate in its original form without refining, or after purifying by high-performance liquid chromatography, or after retaining on a cartridge column for purification of synthetic DNA (e.g., Oligopack SP manufactured by Japan Millipore). The resulting oligonucleotide phosphorothioate was purified with high-performance liquid chromatography as necessary to obtain approximately 1.37 mg of the target 5'-AGCCTCCTTCCCATGCCAGC-3' (SEQ ID NO: 2) (phosphorothioate modified form).

Synthesis Example 2

Synthesis of 5'-CTCACAAACAACATTGCTGA-3' (SEQ ID NO: 3) (Phosphorothioate-modified Form)

Approximately 0.65 mg of the target 5'-CTCACAAACAACATTGCTGA-3' (SEQ ID NO: 3) (phosphorothioate-modified form) were obtained in the same manner as Synthesis Example 1.

Synthesis Example 3

Synthesis of 5'-TGCCAGCCCATCTGCTGGGG-3' (SEQ ID NO: 4) (Phosphorothioate-modified Form)

Approximately 0.98 mg of the target 5'-TGCCAGCCCATCTGCTGGGG-3' (SEQ ID NO: 4) (phosphorothioate-modified form) were obtained in the same manner as Synthesis Example 1.

Synthesis Example 4

Synthesis of 5'-CTCCTGGCAGACTGGTCAGC-3' (SEQ ID NO: 5) (Phosphorothioate-modified Form)

Approximately 1.61 mg of the target 5'-CTCCTGGCAGACTGGTCAGC-3' (SEQ ID NO: 5) (phosphorothioate-modified form) were obtained in the same manner as Synthesis Example 1.

Synthesis Example 5

Synthesis of 5'-TTCCGGAAGCAGGAGAGCTG-3' (SEQ ID NO: 6) (Phosphorothioate-modified Form)

Approximately 1.47 mg of the target 5'-TTCCGGAAGCAGGAGAGCTG-3' (SEQ ID NO: 6) (phosphorothioate-modified form) were obtained in the same manner as Synthesis Example 1.

Synthesis Example 6

Synthesis of 5'-TCCTGGGAATACTGGCACGG-3' (SEQ ID NO: 7) (Phosphorothioate-modified Form)

Approximately 1.64 mg of the target 5'-TCCTGGGAATACTGGCACGG-3' (SEQ ID NO: 7) (phosphorothioate-modified form) were obtained in the same manner as Synthesis Example 1.

Synthesis Example 7

Synthesis of 5'-GCAGCCTCCTTCCCATGCCA-3' (SEQ ID NO: 9) (Phosphorothioate-modified Form)

Approximately 2.47 mg of the target 5'-GCAGCCTCCTTCCCATGCCA-3' (SEQ ID NO: 9) (phosphorothioate-modified form) were obtained in the same manner as Synthesis Example 1.

Synthesis Example 8

Synthesis of 5'-CTCCTTCCCATGCCAGCCCA-3' (SEQ ID NO: 10) (Phosphorothioate-modified Form)

Approximately 2.06 mg of the target 5'-CTCCTTCCCATGCCAGCCCA-3' (SEQ ID NO: 10) (phosphorothioate-modified form) were obtained in the same manner as Synthesis Example 1.

Reference Example 1

Synthesis of 5'-CCCCAGCAGATGGGCTGGCA-3' (SEQ ID NO: 8) (Phosphorothioate-modified Form: Sense Sequence of SEQ ID NO: 4)

Approximately 0.53 mg of the target 5'-CCCCAGCAGATGGGCTGGCA-3' (SEQ ID NO: 8) (phosphorothioate-modified form) were obtained in the same manner as Synthesis Example 1.

Reference Example 2

Synthesis of 5'-GCTGGCATGGGAAGGAGGCT-3' (SEQ ID NO: 11) (Phosphorothioate-modified Form: Sense Sequence of SEQ ID NO: 2)

Approximately 1.91 mg of the target 5'-GCTGGCATGGGAAGGAGGCT-3' (SEQ ID NO: 11)

Experiment 1

Inhibitory Effect on Expression of Human Soluble IL-6R (sIL-6R)

(1) Preparation of CHO.SR344 Cells pBSF2R.236 (Science, 241, 825–828 (1988)) was cleaved with SphI, and the 1205 bp IL-6R cDNA fragment was inserted into mp18 (Amersham). sIL-6R cDNA was prepared by preparing a synthetic oligonucleotide of 5'-ATATTCTAGAGAGCTTCT-3' and using this oligonucleotide in in-vitro mutagenesis system (Amersham). As a result, the termination codon was the 345th of the amino acid sequence.

dhfr-cDNA was inserted into the PvuII site of plasmid pECE (Cell, 45, 721–735 (1986)) to prepare plasmid pECEdhfr. The HindIII-SalI fragment of sIL-6R was inserted into plasmid pECEdhfr to prepare soluble IL-6R expression vector plasmid pECEdhfr344.

pECEdhfr344 was introduced into dhfr-CHO cells DXB-11 (Pro. Natl. Acad. Sci. U.S.A., 77, 4216–4220 (1980)) according to the calcium phosphate method, and amplified with MTX. Finally, 200 nM MTX-resistant sIL-6R-producing CHO cells (CHO.SR344) were prepared (J. Biochem., 108, 673–676 (1990)). Ordinary culturing of the cells was performed in IMDM medium (Gibco) containing 5% FCS (Xavier Investments) and 200 nM MTX.

(2) Effect of IL-6R Antisense Oligonucleotides on sIL-6R Production of CHO.SR344 Cells The CHO.SR344 cells were peeled from the culture dish with trypsin-EDTA (Gibco). After washing with culture liquid, the cells were additionally washed with Non-Serum (trade name) serum-free medium and suspended in, Non-Serum, serum-free medium containing 200 nM MTX. 100 µl of CHO.SR344 cell suspension ($5\times10^4$ cells/ml) and 100 µl of 2 µM IL-6R antisense oligonucleotide were added to a 96-well culture plate followed by culturing in an incubator at 37° C. and 5% $CO_2$.

After culturing for 24 hours, the amount of soluble IL-6R in the culture supernatant was measured by sandwich ELISA using mouse anti-IL-6R monoclonal antibody (MT18) (Japanese Unexamined Patent Publication No. 2-288898) and rabbit anti-IL-6R polyclonal antibody. Furthermore, the sense oligonucleotide derivative to SEQ ID NO: 4 (SEQ ID NO: 8) or the sense oligonucleotide to SEQ ID NO: 2 (SEQ ID NO: 11) were measured as controls.

The human IL-6R antisense oligonucleotide exhibited inhibitory effects on expression of soluble IL-6R (FIGS. 1 and 2).

---

What is claimed is:

1. An inhibitor of expression of human IL-6 receptor comprising an optionally modified antisense oligonucleotide wherein said antisense oligonucleotide has a nucleotide sequence selected from the group consisting of CTCACAAACA ACATTGCTGA (SEQ ID NO:3),
CTCCTGGCAG ACTGGTCAGC (SEQ ID NO:5),
TTCCGGAAGC AGGAGAGCTG (SEQ ID NO:6), and
TCCTGGGAAT ACTGGCACGG (SEQ ID NO:7).

2. An inhibitor of expression of human IL-6 receptor comprising an antisense oligonucleotide wherein said antisense oligonucleotide has a nucleotide sequence selected from the group consisting of CTCACAAACA ACATTGCTGA (SEQ ID NO:3),
CTCCTGGCAG ACTGGTCAGC (SEQ ID NO:5),
TTCCGGAAGC AGGAGAGCTG (SEQ ID NO:6), and
TCCTGGGAAT ACTGGCACGG (SEQ ID NO:7).

3. The inhibitor of claim 2, wherein said antisense oligonucleotide has a nucleotide sequence

CTCACAAACA ACATTGCTGA (SEQ ID NO:3).

4. The inhibitor of claim 2, wherein said antisense oligonucleotide has a nucleotide sequence

CTCCTGGCAG ACTGGTCAGC (SEQ ID NO:5).

5. The inhibitor of claim 2, wherein said antisense oligonucleotide has a nucleotide sequence

TTCCGGAAGC AGGAGAGCTG (SEQ ID NO:6).

6. The inhibitor of claim 2, wherein said antisense oligonucleotide has a nucleotide sequence

TCCTGGGAAT ACTGGCACGG (SEQ ID NO:7).

7. An inhibitor of expression of human IL-6 receptor comprising an antisense oligonucleotide, said antisense oligonucleotide having the structure:

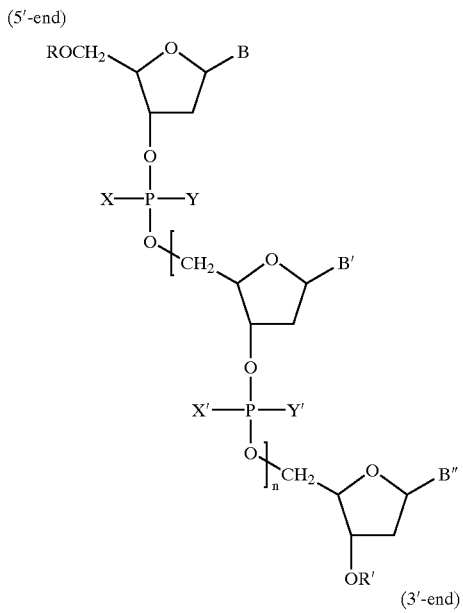

wherein X and X' are independently sulfur, a lower alkyl group, a primary amine, a secondary amine, or a lower alkoxy;
Y and Y' are independently oxygen or sulfur;
B, B' and B" are independently adenine, guanine, thymine or cytosine;
R and R' are independently hydrogen, dimethoxytrityl or a lower alkyl group; and n is from 7 to 28, further wherein said antisense oligonucleotide has a nucleotide sequence selected from the group consisting of:

CTCACAAACA ACATTGCTGA (SEQ ID NO:3),
CTCCTGGCAG ACTGGTCAGC (SEQ ID NO:5),
TTCCGGAAGC AGGAGAGCTG (SEQ ID NO:6), and
TCCTGGGAAT ACTGGCACGG (SEQ ID NO:7).

8. The inhibitor of claim 7, wherein said antisense oligonucleotide has a nucleotide sequence

CTCACAAACA ACATTGCTGA (SEQ ID NO:3).

9. The inhibitor of claim 7, wherein said antisense oligonucleotide has a nucleotide sequence

CTCCTGGCAG ACTGGTCAGC (SEQ ID NO:5).

10. The inhibitor of claim 7, wherein said antisense oligonucleotide has a nucleotide sequence

TTCCGGAAGC AGGAGAGCTG (SEQ ID NO:6).

11. The inhibitor of claim 7, wherein said antisense oligonucleotide has a nucleotide sequence

TCCTGGGAAT ACTGGCACGG (SEQ ID NO:7).

12. An optionally modified oligonucleotide for inhibiting expression of human IL-6 receptor, wherein said oligonucleotide is up to 30 nucleotides in length and includes a nucleotide sequence selected from the group consisting of CTCACAAACA ACATTGCTGA (SEQ ID NO:3),
CTCCTGGCAG ACTGGTCAGC (SEQ ID NO:5),
TTCCGGAAGC AGGAGAGCTG (SEQ ID NO:6), and
TCCTGGGAAT ACTGGCACGG (SEQ ID NO:7).

13. The oligonucleotide of claim 12, wherein said oligonucleotide is modified with a member selected from the group consisting of alkylphosphonate, phosphorothioate, phosphorothioate, phosphoroamidate and phosphate triester.

14. The oligonucleotide of claim 13, wherein said oligonucleotide is modified with an alkylphosphonate.

15. The oligonucleotide of claim 13, wherein said oligonucleotide is modified with a phosphorothioate.

16. The oligonucleotide of claim 13, wherein said oligonucleotide is modified with a phosphorodithioate.

17. The oligonucleotide of claim 13, wherein said oligonucleotide is modified with a phosphoroamidate.

18. The oligonucleotide of claim 13, wherein said oligonucleotide is modified with a phosphate triester.

19. The oligonucleotide of claim 14, wherein said alkylphosphonate is a methylphosphonate.

20. The oligonucleotide of claim 14, wherein said alkylphosphonate is an ethylphosphonate.

21. A method for inhibiting expression of human IL-6 receptor comprising:

a) providing to a human cell the oligonucleotide of claim 12; and b) contacting said cell with said oligonucleotide under conditions such that said oligonucleotide is delivered into said cell and hybridizes with a nucleic acid sequence encoding the IL-6 receptor of said cell, so that the human IL-6 receptor of said cell is inhibited.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 3319 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 438..1844

(xi) SEQUENCE DESCRIPTION: SEQ ID NO:1:

```
GGCGGTCCCC TGTTCTCCCC GCTCAGGTGC GGCGCTGTGG CAGGAAGCCA CCCCCTCGGT    60

CGGCCGGTGC GCGGGGCTGT TGCGCCATCC GCTCCGGCTT TCGTAACCGC ACCCTGGGAC   120

GGCCCAGAGA CGCTCCAGCG CGAGTTCCTC AAATGTTTTC CTGCGTTGCC AGGACCGTCC   180

GCCGCTCTGA GTCATGTGCG AGTGGGAAGT CGCACTGACA CTGAGCCGGG CCAGAGGGAG   240

AGGAGCCGAG CGCGGCGCGG GGCCGAGGGA CTCGCAGTGT GTGTAGAGAG CCGGGCTCCT   300

GCGGATGGGG GCTGCCCCCG GGGCCTGAGC CCGCCTGCCC GCCCACCGCC CCGCCCCGCC   360

CCTGCCACCC CTGCCGCCCG GTTCCCATTA GCCTGTCCGC CTCTGCGGGA CCATGGAGTG   420

GTAGCCGAGG AGGAAGC ATG CTG GCC GTC GGC TGC GCG CTG CTG GCT GCC     470
                   Met Leu Ala Val Gly Cys Ala Leu Leu Ala Ala
                    1               5                  10

CTG CTG GCC GCG CCG GGA GCG GCG CTG GCC CCA AGG CGC TGC CCT GCG    518
Leu Leu Ala Ala Pro Gly Ala Ala Leu Ala Pro Arg Arg Cys Pro Ala
```

|  |  |  |  |  |  |  |  |  |  |  |  |  |  |
|---|---|---|---|---|---|---|---|---|---|---|---|---|---|
|  |  |  | 15 |  |  |  | 20 |  |  |  | 25 |  |  |
| CAG | GAG | GTG | GCA | AGA | GGC | GTG | CTG | ACC | AGT | CTG | CCA | GGA | GAC AGC GTG |
| Gln | Glu | Val | Ala | Arg | Gly | Val | Leu | Thr | Ser | Leu | Pro | Gly | Asp Ser Val |
|  |  | 30 |  |  |  |  | 35 |  |  |  |  | 40 |  |

566

ACT CTG ACC TGC CCG GGG GTA GAG CCG GAA GAC AAT GCC ACT GTT CAC    614
Thr Leu Thr Cys Pro Gly Val Glu Pro Glu Asp Asn Ala Thr Val His
     45                 50                  55

TGG GTG CTC AGG AAG CCG GCT GCA GGC TCC CAC CCC AGC AGA TGG GCT    662
Trp Val Leu Arg Lys Pro Ala Ala Gly Ser His Pro Ser Arg Trp Ala
 60              65                  70                      75

GGC ATG GGA AGG AGG CTG CTG CTG AGG TCG GTG CAG CTC CAC GAC TCT    710
Gly Met Gly Arg Arg Leu Leu Leu Arg Ser Val Gln Leu His Asp Ser
             80                  85                  90

GGA AAC TAT TCA TGC TAC CGG GCC GGC CGC CCA GCT GGG ACT GTG CAC    758
Gly Asn Tyr Ser Cys Tyr Arg Ala Gly Arg Pro Ala Gly Thr Val His
                 95                 100                 105

TTG CTG GTG GAT GTT CCC CCC GAG GAG CCC CAG CTC TCC TGC TTC CGG    806
Leu Leu Val Asp Val Pro Pro Glu Glu Pro Gln Leu Ser Cys Phe Arg
             110                 115                 120

AAG AGC CCC CTC AGC AAT GTT GTT TGT GAG TGG GGT CCT CGG AGC ACC    854
Lys Ser Pro Leu Ser Asn Val Val Cys Glu Trp Gly Pro Arg Ser Thr
         125                 130                 135

CCA TCC CTG ACG ACA AAG GCT GTG CTC TTG GTG AGG AAG TTT CAG AAC    902
Pro Ser Leu Thr Thr Lys Ala Val Leu Leu Val Arg Lys Phe Gln Asn
140             145                 150                 155

AGT CCG GCC GAA GAC TTC CAG GAG CCG TGC CAG TAT TCC CAG GAG TCC    950
Ser Pro Ala Glu Asp Phe Gln Glu Pro Cys Gln Tyr Ser Gln Glu Ser
                 160                 165                 170

CAG AAG TTC TCC TGC CAG TTA GCA GTC CCG GAG GGA GAC AGC TCT TTC    998
Gln Lys Phe Ser Cys Gln Leu Ala Val Pro Glu Gly Asp Ser Ser Phe
             175                 180                 185

TAC ATA GTG TCC ATG TGC GTC GCC AGT AGT GTC GGG AGC AAG TTC AGC   1046
Tyr Ile Val Ser Met Cys Val Ala Ser Ser Val Gly Ser Lys Phe Ser
         190                 195                 200

AAA ACT CAA ACC TTT CAG GGT TGT GGA ATC TTG CAG CCT GAT CCG CCT   1094
Lys Thr Gln Thr Phe Gln Gly Cys Gly Ile Leu Gln Pro Asp Pro Pro
     205                 210                 215

GCC AAC ATC ACA GTC ACT GCC GTG GCC AGA AAC CCC CGC TGG CTC AGT   1142
Ala Asn Ile Thr Val Thr Ala Val Ala Arg Asn Pro Arg Trp Leu Ser
220             225                 230                 235

GTC ACC TGG CAA GAC CCC CAC TCC TGG AAC TCA TCT TTC TAC AGA CTA   1190
Val Thr Trp Gln Asp Pro His Ser Trp Asn Ser Ser Phe Tyr Arg Leu
                 240                 245                 250

CGG TTT GAG CTC AGA TAT CGG GCT GAA CGG TCA AAG ACA TTC ACA ACA   1238
Arg Phe Glu Leu Arg Tyr Arg Ala Glu Arg Ser Lys Thr Phe Thr Thr
             255                 260                 265

TGG ATG GTC AAG GAC CTC CAG CAT CAC TGT GTC ATC CAC GAC GCC TGG   1286
Trp Met Val Lys Asp Leu Gln His His Cys Val Ile His Asp Ala Trp
         270                 275                 280

AGC GGC CTG AGG CAC GTG GTG CAG CTT CGT GCC CAG GAG GAG TTC GGG   1334
Ser Gly Leu Arg His Val Val Gln Leu Arg Ala Gln Glu Glu Phe Gly
     285                 290                 295

CAA GGC GAG TGG AGC GAG TGG AGC CCG GAG GCC ATG GGC ACG CCT TGG   1382
Gln Gly Glu Trp Ser Glu Trp Ser Pro Glu Ala Met Gly Thr Pro Trp
300             305                 310                 315

ACA GAA TCC AGG AGT CCT CCA GCT GAG AAC GAG GTG TCC ACC CCC ATG   1430
Thr Glu Ser Arg Ser Pro Pro Ala Glu Asn Glu Val Ser Thr Pro Met
                 320                 325                 330

CAG GCA CTT ACT ACT AAT AAA GAC GAT GAT AAT ATT CTC TTC AGA GAT   1478

```
                    Gln Ala Leu Thr Thr Asn Lys Asp Asp Asp Asn Ile Leu Phe Arg Asp
                                    335                 340                 345

TCT GCA AAT GCG ACA AGC CTC CCA GTG CAA GAT TCT TCT TCA GTA CCA                 1526
Ser Ala Asn Ala Thr Ser Leu Pro Val Gln Asp Ser Ser Ser Val Pro
        350                 355                 360

CTG CCC ACA TTC CTG GTT GCT GGA GGG AGC CTG GCC TTC GGA ACG CTC                 1574
Leu Pro Thr Phe Leu Val Ala Gly Gly Ser Leu Ala Phe Gly Thr Leu
365                 370                 375

CTC TGC ATT GCC ATT GTT CTG AGG TTC AAG AAG ACG TGG AAG CTG CGG                 1622
Leu Cys Ile Ala Ile Val Leu Arg Phe Lys Lys Thr Trp Lys Leu Arg
380                 385                 390                 395

GCT CTG AAG GAA GGC AAG ACA AGC ATG CAT CCG CCG TAC TCT TTG GGG                 1670
Ala Leu Lys Glu Gly Lys Thr Ser Met His Pro Pro Tyr Ser Leu Gly
                400                 405                 410

CAG CTG GTC CCG GAG AGG CCT CGA CCC ACC CCA GTG CTT GTT CCT CTC                 1718
Gln Leu Val Pro Glu Arg Pro Arg Pro Thr Pro Val Leu Val Pro Leu
            415                 420                 425

ATC TCC CCA CCG GTG TCC CCC AGC AGC CTG GGG TCT GAC AAT ACC TCG                 1766
Ile Ser Pro Pro Val Ser Pro Ser Ser Leu Gly Ser Asp Asn Thr Ser
        430                 435                 440

AGC CAC AAC CGA CCA GAT GCC AGG GAC CCA CGG AGC CCT TAT GAC ATC                 1814
Ser His Asn Arg Pro Asp Ala Arg Asp Pro Arg Ser Pro Tyr Asp Ile
    445                 450                 455

AGC AAT ACA GAC TAC TTC TTC CCC AGA TAG CTGGCTGGGT GGCACCAGCA                   1864
Ser Asn Thr Asp Tyr Phe Phe Pro Arg  *
460                 465

GCCTGGACCC TGTGGATGAC AAAACACAAA CGGGCTCAGC AAAAGATGCT TCTCACTGCC               1924

ATGCCAGCTT ATCTCAGGGG TGTGCGGCCT TTGGCTTCAC GGAAGAGCCT TGCGGAAGGT               1984

TCTACGCCAG GGAAAATCA GCCTGCTCCA GCTGTTCAGC TGGTTGAGGT TTCAAACCTC                2044

CCTTTCCAAA TGCCCAGCTT AAAGGGGTTA GAGTGAACTT GGGCCACTGT GAAGAGAACC               2104

ATATCAAGAC TCTTTGGACA CTCACACGGA CACTCAAAAG CTGGGCAGGT TGGTGGGGGC               2164

CTCGGTGTGG AGAAGCGGCT GGCAGCCCAC CCCTCAACAC CTCTGCACAA GCTGCACCCT               2224

CAGGCAGGTG GGATGGATTT CCAGCCAAAG CCTCCTCCAG CCGCCATGCT CCTGGCCCAC               2284

TGCATCGTTT CATCTTCCAA CTCAAACTCT TAAAACCCAA GTGCCCTTAG CAAATTCTGT               2344

TTTTCTAGGC CTGGGACGG CTTTTACTTA AACGCCAAGG CCTGGGGAA GAAGCTCTCT                 2404

CCTCCCTTTC TTCCCTACAG TTCAAAAACA GCTGAGGGTG AGTGGGTGAA TAATACAGTA               2464

TGTCAGGGCC TGGTCGTTTT CAACAGAATT ATAATTAGTT CCTCATTAGC AGTTTTGCCT               2524

AAATGTGAAT GATGATCCTA GGCATTTGCT GAATACAGAG GCAACTGCAT GGCTTTGGG                2584

TTGCAGGACC TCAGGTGAGA AGCAGAGGAA GGAGAGGAGA GGGGCACAGG GTCTCTACCA               2644

TCCCCTGTAG AGTGGGAGCT GAGTGGGGGA TCACAGCCTC TGAAAACCAA TGTTCTCTCT               2704

TCTCCACCTC CCACAAAGGA GAGCTAGCAG CAGGGAGGGC TTCTGCCATT TCTGAGATCA               2764

AAACGGTTTT ACTGCAGCTT TGTTTGTTGT CAGCTGAACC TGGGTAACTA GGGAAGATAA               2824

TATTAAGGAA GACAATGTGA AAAGAAAAAT GAGCCTGGCA AGAATGCGTT TAAACTTGGT               2884

TTTTAAAAAA CTGCTGACTG TTTTCTCTTG AGAGGGTGGA ATATCCAATA TTCGCTGTGT               2944

CAGCATAGAA GTAACTTACT TAGGTGTGGG GGAAGCACCA TAACTTTGTT TAGCCCAAAA               3004

CCAAGTCAAG TGAAAAGGA GGAAGAGAAA AAATATTTTC CTGCCAGGCA TGGAGGCCCA                3064

CGCACTTCGG GAGGTCGAGG CAGGAGGATC ACTTGAGTCC AGAAGTTTGA GATCAGCCTG               3124

GGCAATGTGA TAAAACCCCA TCTCTACAAA AAGCATAAAA ATTAGCCAAG TGTGGTAGAG               3184
```

```
TGTGCCTGAA GTCCCAGATA CTTGGGGGGC TGAGGTGGGA GGATCTCTTG AGCCTGGGAG      3244

GTCAAGGCTG CAGTGAGCCG AGATTGCACC ACTGCACTCC AGCCTGGGGT GACAGAGCAA      3304

GTGAGACCCT GTCTC                                                      3319
```

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

```
AGCCTCCTTC CCATGCCAGC                                                   20
```

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
CTCACAAACA ACATTGCTGA                                                   20
```

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

```
TGCCAGCCCA TCTGCTGGGG                                                   20
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:

```
CTCCTGGCAG ACTGGTCAGC                                                   20
```

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

```
TTCCGGAAGC AGGAGAGCTG                                                      20

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

TCCTGGGAAT ACTGGCACGG                                                      20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CCCCAGCAGA TGGGCTGGCA                                                      20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GCAGCCTCCT TCCCATGCCA                                                      20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:10:

CTCCTTCCCA TGCCAGCCCA                                                      20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GCTGGCATGG GAAGGAGGCT                                                      20
```